(12) United States Patent
Italiaie

(10) Patent No.: US 10,687,858 B2
(45) Date of Patent: *Jun. 23, 2020

(54) SPINAL IMPLANT SYSTEM AND METHODS OF USE

(71) Applicant: Warsaw Orthopedic, Inc., Warsaw, IN (US)

(72) Inventor: Christel Italiaie, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/184,552

(22) Filed: Nov. 8, 2018

(65) Prior Publication Data

US 2020/0146724 A1 May 14, 2020

(51) Int. Cl.
*A61B 17/70* (2006.01)

(52) U.S. Cl.
CPC ...... *A61B 17/7035* (2013.01); *A61B 17/7032* (2013.01); *A61B 17/7002* (2013.01)

(58) Field of Classification Search
CPC ............ A61B 17/7032; A61B 17/7035; A61B 17/863; A61B 17/7002; A61B 2017/564
USPC ................................. 606/264–272, 305, 308
See application file for complete search history.

(56) References Cited

U.S. PATENT DOCUMENTS

| | | | |
|---|---|---|---|
| 5,885,286 A | 3/1999 | Sherman et al. | |
| 6,565,566 B1 | 5/2003 | Wagner et al. | |
| 8,167,910 B2 | 5/2012 | Nilsson | |
| 8,197,518 B2 | 6/2012 | Harrill, Sr. et al. | |
| 8,298,265 B2 | 10/2012 | Purcell et al. | |
| 8,298,275 B2 | 10/2012 | Rezach | |
| 8,304,089 B1 | 11/2012 | Song et al. | |
| 9,775,660 B2* | 10/2017 | Spratt | A61B 17/8685 |
| 9,993,270 B2* | 6/2018 | Butler | A61B 17/7035 |
| 10,335,201 B2* | 7/2019 | Rezach | A61B 17/7032 |
| 2007/0270839 A1 | 11/2007 | Jeon et al. | |
| 2008/0108992 A1 | 5/2008 | Barry et al. | |
| 2011/0093021 A1 | 4/2011 | Fanger et al. | |
| 2011/0098755 A1* | 4/2011 | Jackson | A61B 17/8605 606/305 |

(Continued)

FOREIGN PATENT DOCUMENTS

WO 2005037067 A2 4/2005

OTHER PUBLICATIONS

International Search Report and Written Opinion of the International Searching Authority, Korean Intellectual Property Office, PCT/2019/055816, dated Feb. 4, 2020.

*Primary Examiner* — Eduardo C Robert
*Assistant Examiner* — David C Comstock

(57) ABSTRACT

A bone fastener comprises a first member defining an implant cavity and a first groove. A first band is disposable in the first groove. A base is connectable with the first member and engageable with the first band. The base defines a second groove and a slot. A second band is disposable in the second groove and defines an opening aligned with the slot. A second member is connectable with the base and engageable with the second band. The second member is configured to penetrate tissue. The opening is aligned with the slot to facilitate an angular range of movement of the second member relative to the first member. Implants, spinal constructs, systems, instruments and methods are disclosed.

19 Claims, 11 Drawing Sheets

(56) References Cited

U.S. PATENT DOCUMENTS

| | | |
|---|---|---|
| 2012/0143266 A1* | 6/2012 | Jackson ............. A61B 17/7008 606/328 |
| 2012/0197313 A1* | 8/2012 | Cowan ............... A61B 17/7037 606/305 |
| 2013/0110180 A1* | 5/2013 | Doubler ............. A61B 17/7037 606/308 |
| 2013/0218213 A1* | 8/2013 | Lemoine ............ A61B 17/7032 606/305 |
| 2014/0257411 A1 | 9/2014 | Rezach |
| 2015/0282844 A1* | 10/2015 | Vedula .............. A61B 17/7032 606/305 |
| 2016/0331413 A1* | 11/2016 | Daniels ............. A61B 17/7032 |
| 2017/0245898 A1* | 8/2017 | May ................... A61B 17/7037 |
| 2018/0110548 A1 | 4/2018 | May et al. |
| 2018/0206890 A1 | 7/2018 | Rezach |
| 2019/0175224 A1* | 6/2019 | Doubler ............. A61B 17/7032 |
| 2019/0247096 A1* | 8/2019 | Kim ....................... A61B 17/70 |

* cited by examiner

SPINAL IMPLANT SYSTEM AND METHODS OF USE

TECHNICAL FIELD

The present disclosure generally relates to medical devices for the treatment of spinal disorders, and more particularly to a surgical implant system including a bone fastener and related methods.

BACKGROUND

Spinal pathologies and disorders such as kyphosis, scoliosis and other curvature abnormalities, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior technologies.

SUMMARY

In one embodiment, a bone fastener is provided. The bone fastener comprises a first member defining an implant cavity and a first groove. A first band is disposable in the first groove. A base is connectable with the first member and engageable with the first band. The base defines a second groove and a slot. A second band is disposable in the second groove and defines an opening aligned with the slot. A second member is connectable with the base and engageable with the second band. The second member is configured to penetrate tissue. The opening is aligned with the slot to facilitate an angular range of movement of the second member relative to the first member. In some embodiments, implants, spinal constructs, systems, instruments and methods are disclosed.

In one embodiment, the bone fastener comprises a first member defining an implant cavity and a first groove. A first band is disposable in the first groove. A part is disposed within the implant cavity. A base is connectable with the first member and engageable with the first band. The base defines a second groove and a slot. A second band is disposable in the second groove and defines an opening aligned with the slot. A second member is connectable with the base and engageable with the second band. The second member is configured to penetrate tissue. A third band is disposed with the base. The part is engageable with the third band to fix the base with the second member. The opening is aligned with the slot to facilitate an angular range of movement of the second member relative to the first member.

In one embodiment, the bone fastener comprises a spinal rod receiver defining a first groove. A first band is disposable in the first groove. A base is connectable with the receiver and engageable with the first band. The base defines a second groove and a slot. A second band is disposable in the second groove and defines an opening aligned with the slot. A screw shaft is connectable with the base and engageable with the second band. The opening is aligned with the slot and the screw shaft is movable in the slot to a selected angulation relative to the receiver.

BRIEF DESCRIPTION OF THE DRAWINGS

The present disclosure will become more readily apparent from the specific description accompanied by the following drawings, in which.

DETAILED DESCRIPTION

Figure 1:
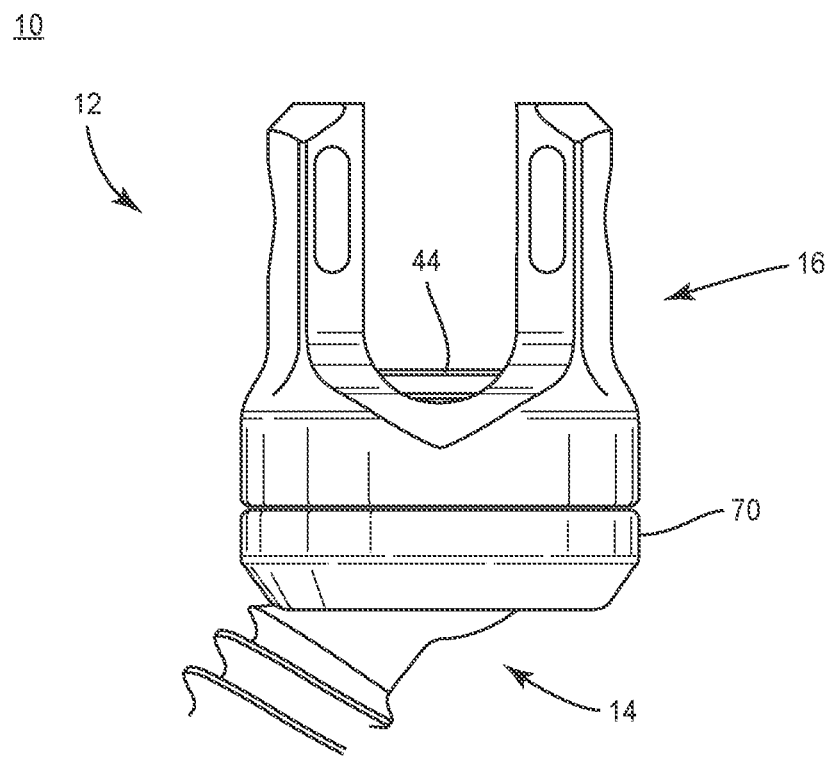
FIG. 1 is a side view of components of one embodiment of a spinal implant system in accordance with the principles of the present disclosure.

The exemplary embodiments of a surgical system and related methods of use disclosed are discussed in terms of medical devices for the treatment of musculoskeletal disorders and more particularly, in terms of a spinal implant system including a bone fastener. In some embodiments, the spinal implant system includes an implant comprising a bone fastener, such as, for example, a pedicle bone screw. In some embodiments, the spinal implant system includes a selectively coupled pedicle screw system that allows for operating room back-table assembly of a bone fastener without use of instrumentation. In some embodiments, the systems and methods of the present disclosure are employed with a spinal joint fusion or fixation procedure, for example, with a cervical, thoracic, lumbar and/or sacral region of a spine.

In some embodiments, the present spinal implant system comprises a spinal implant, such as, for example, a bone screw that is engageable with tissue surfaces of one or more vertebral levels. In some embodiments, the spinal implant system includes a selectively coupled pedicle screw system that allows for a biased angle configuration. In some embodiments, the bone fastener provides a range of angulation to allow the receiver to be positioned in a relaxed or non-stressed orientation relative to the screw shaft. In some embodiments, this configuration allows the receivers of adjacent bone fasteners to be disposed in a relatively parallel orientation. In some embodiments, the spinal implant system comprises a bone fastener configured for angulation in a cephalad-caudal direction of a patient body. In some embodiments, the screw shaft is configured for an angulation in a range of approximately 0 through 40 degrees relative to the receiver. In some embodiments, the spinal implant system comprises a screw head, a crown, a base, a head-base ring, a crown ring, and bone screw shaft ring and a bone screw shaft. In some embodiments, the spinal implant system includes slots or rocker holes configured to facilitate connection with a surgical instrument.

In some embodiments, the screw head includes a 4.75 mm biased angle thread-form. In some embodiments, the screw head includes a receiver configured to capture a 4.75 mm spinal rod. In some embodiments, the screw head includes a temporary crown retention slot and/or ramp. In some embodiments, the screw head includes a base retaining slot. In some embodiments, the spinal implant system includes ring slots to facilitate a manual engagement of the receiver and the screw shaft. In some embodiments, the base includes a biased angle slot. In some embodiments, the base includes a bone screw shaft ring slot configured to resist and/or prevent the screw ring from rotation.

In some embodiments, the spinal implant system comprises a crown having a flat top, knurled features and mating features to facilitate positioning with the screw head. In some embodiments, the crown includes a cavity configured for disposal of the screw shaft. In some embodiments, the crown includes planar surfaces configured for keyed connection with the screw head. In some embodiments, the planar surfaces are utilized to position the biased angle feature on the base.

In some embodiments, the bone screw shaft ring includes a thickness. In some embodiments, the bone screw shaft ring includes two chamfers. In some embodiments, the bone screw shaft ring includes a cavity. In some embodiments, the cavity is configured to facilitate axial translation of the bone screw shaft ring relative to the base. In some embodiments, the cavity is engageable with the base to resist and/or prevent rotation of the bone screw shaft ring such that the bone screw shaft ring slot is positioned in alignment with the biased angle slot of the base. In some embodiments, the bone screw shaft ring includes a bending notch configured to reduce a force required to engage the screw head with the bone screw shaft. In some embodiments, the bone screw shaft ring slot is configured to allow angulation of the bone screw shaft at approximately 40 degrees. In some embodiments, the bone screw shaft ring slot and the biased angle slot can be rotated 360 degrees about the bone screw shaft.

In some embodiments, the bone screw includes a base having notches configured for engagement with ends of the bone screw shaft ring to resist and/or prevent disengagement of the bone screw shaft ring from the base. In some embodiments, engagement of the bone screw shaft ring with surfaces of the notches allows for axial translation of the bone screw shaft ring relative to the base while resisting and/or preventing rotation of the bone screw shaft ring relative to the base to maintain alignment of an opening of the bone screw shaft ring with the biased angle slot.

In some embodiments, the spinal implant system comprises a modular screw system. In some embodiments, the spinal implant system comprises a modular screw system including screw shaft assemblies and implant receiver/head assemblies that may be joined together during manufacturing or intra-operatively, such as, for example, during a surgical procedure in an operating room.

In some embodiments, the spinal implant system comprises a modular system that includes a bone fastener including an array of selectively coupled members, such as bone screw shafts and receivers. In some embodiments, the spinal implant system comprises a selectively coupled bone fastener that can be assembled on a surgical table or in-situ. In some embodiments, the selectively coupled bone fastener is assembled with a force of less than 50 Newtons (N). In some embodiments, the bone fastener is selectively coupled with a non-instrumented assembly. In some embodiments, the non-instrumented assembly comprises manually engaging a screw shaft with a body. In some embodiments, the non-instrumented assembly comprises manually engaging the screw shaft in a pop-on engagement with a body. In some embodiments, a force required to manually engage a screw shaft with a body in a non-instrumented assembly is in a range of 2 to 50 N. In some embodiments, a force required to manually engage a screw shaft with a body in a non-instrumented assembly is in a range of 5 to 10 N. In some embodiments, a screw shaft is manually engaged with a body in a non-instrumented assembly, as described herein, such that removal of a body from the screw shaft requires a force and/or a pull-out strength of at least 5000 N. In some embodiments, this configuration provides manually engageable components of a bone fastener that are assembled without instrumentation, and subsequent to assembly, the assembled components have a selected pull-out strength and/or can be pulled apart, removed and/or separated with a minimum required force.

In some embodiments, the bone fastener is configured for assembly without the use of an instrument, such as, for example, a practitioner, surgeon and/or medical staff utilizes their hands for assembly. In some embodiments, the system requires minimal force to attach a body and a screw shaft assembly in-situ thereby reducing a pre-load on the vertebrae, such as, for, example, the pedicle.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, postero-lateral, and/or antero-lateral approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a bone fastener, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-7, there are illustrated components of a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 includes a spinal implant, such as, for example, a bone fastener 12. Bone fastener 12 comprises a member, such as, for example, a screw shaft 14 and a member, such as, for example, a spinal rod receiver 16. Bone fastener 12 includes a base 70 having a recess 88 disposed in alignment with an opening 90 of a screw shaft retaining ring 86 to facilitate an angular range of movement of screw shaft 14 relative to receiver 16, as described herein. In some embodiments, screw shaft 14, base 70 and receiver 16 are assembled in situ or prior to implant to form bone fastener 12, as described herein.

Receiver 16 extends along and defines an axis X1. Receiver 16 includes a pair of spaced apart arms 18, 20 that define an implant cavity 22 therebetween configured for disposal of a component of a spinal construct, such as, for example, a spinal rod 200. Arms 18, 20 each extend parallel to axis X1. In some embodiments, arm 18 and/or arm 20 may be disposed at alternate orientations, relative to axis X1, such as, for example, transverse, perpendicular and/or other angular orientations such as acute or obtuse, coaxial and/or may be offset or staggered. Arms 18, 20 each include an arcuate outer surface extending between a pair of side surfaces. At least one of the outer surfaces and the side surfaces of arms 18, 20 have at least one recess or cavity therein configured to receive an insertion tool, compression instrument and/or instruments for inserting and tensioning bone fastener 12. In some embodiments, arms 18, 20 are connected at proximal and distal ends thereof such that receiver 16 defines a closed spinal rod slot.

Cavity 22 is substantially U-shaped. In some embodiments, all or only a portion of cavity 22 may have alternate cross section configurations, such as, for example, closed, V-shaped, W-shaped, oval, oblong triangular, square, polygonal, irregular, uniform, non-uniform, offset, staggered, and/or tapered. Receiver 16 includes an inner surface 24. A portion of surface 24 includes a thread form 26 located adjacent arm 18 and adjacent arm 20. In some embodiments, thread form 26 includes a 4.75 mm biased angle. Thread form 26 is configured for engagement with a coupling member, such as, for example, a setscrew (not shown), to retain the spinal rod within cavity 22. In some embodiments, surface 24 may be disposed with the coupling member in alternate fixation configurations, such as, for example, friction fit, pressure fit, locking protrusion/recess, locking keyway and/or adhesive. In some embodiments, all or only a portion of surface 24 may have alternate surface configurations to enhance engagement with the spinal rod and/or the setscrew, such as, for example, rough, arcuate, undulating, mesh, porous, semi-porous, dimpled and/or textured. In some embodiments, receiver 16 may include alternate configurations, such as, for example, closed, open and/or side access.

Receiver 16 includes a surface 30 that defines a cavity, such as, for example, a groove 34. Groove 34 is configured for disposal of a band, such as, for example, a circumferential ring 36. Groove 34 includes a circumferential channel 38 that accommodates expansion of ring 36. Ring 36 includes a circumference that extends between ends of ring 36. In some embodiments, the ends define a gap. In some embodiments, the gap is sized such that the gap has a thickness that is less than the height and the width. In some embodiments, upon disposal of ring 36 with groove 34, the surface of groove 34 resists and/or prevents axial translation of ring 36 relative to axis X1.

Ring 36 is expandable and resilient between a contracted and/or capture orientation, and an expanded orientation, as described herein. Ring 36 facilitates manual assembly of receiver 16 with base 70 in a non-instrumented assembly, as described herein. In some embodiments, ring 36 is expandable and resilient between a contracted and/or capture orientation and an expanded orientation for assembly of receiver 16 with base 70.

Receiver 16 includes a surface 40 configured for disposal of a part, such as, for example, a crown 44, as described herein. In some embodiments, all or only a portion of surface 40 may have alternate surface configurations, such as, for example, rough, arcuate, undulating, mesh, porous, semi-porous, dimpled and/or textured. Crown 44 is configured for disposal within cavity 22 and engagement with surface 40.

Crown 44 includes a wall 50 having an end surface 52 and an end surface 54. Surface 52 is configured to define at least a portion of cavity 22. Surface 52 defines a curved portion of crown 44 configured for engagement with the spinal rod. In some embodiments, all or only a portion of surface 52 may have alternate cross section configurations, such as, for example, oval, oblong triangular, square, polygonal, irregular, uniform, non-uniform, offset, staggered, and/or tapered. Wall 50 defines a receiver engagement portion, such as, for example, a flange 58 configured for a provisional mating engagement with a portion of surface 40. For example, when the spinal rod is disposed with receiver 16, the spinal rod causes flange 58 to disengage from surface 40 and translate over a ramp 42 to facilitate axial translation of crown 44 relative to receiver 16, as described herein. In some embodiments, surface 52 includes a plurality of ridges 59 configured to improve purchase of crown 44 with the spinal rod.

Figure 3:
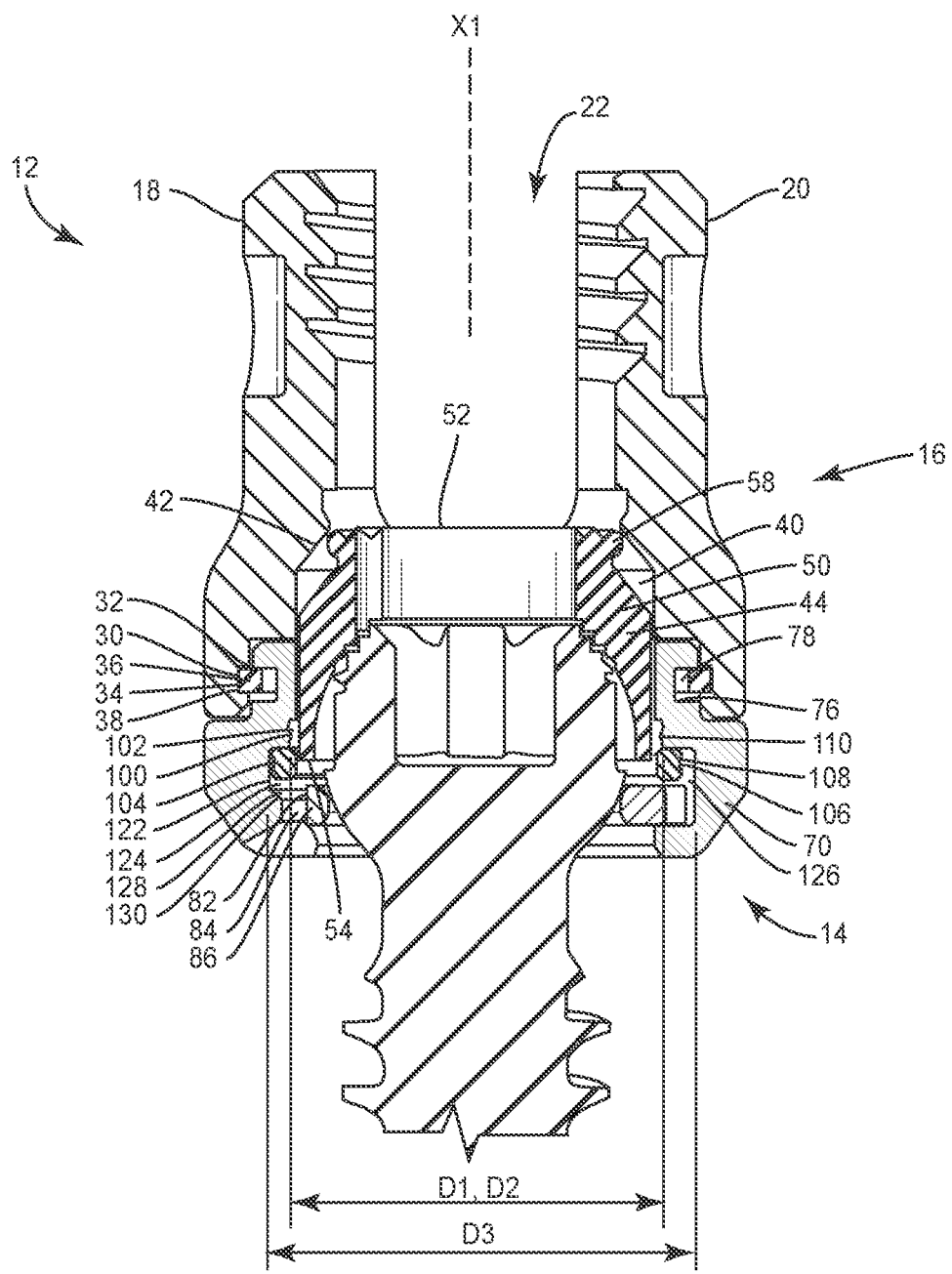
FIG. 3 is a cross section view of the components shown in FIG. 1.
Figure 4:
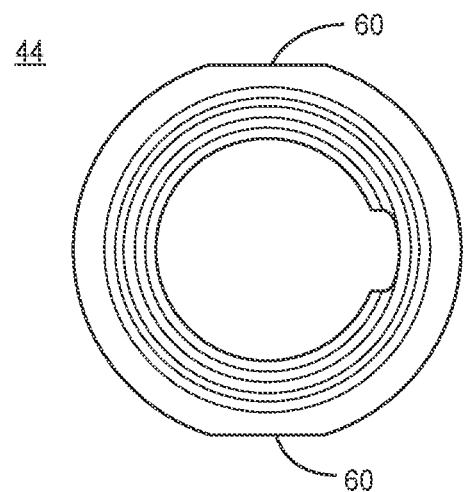
FIG. 4 is a side view of components shown in FIG. 1.

Crown 44 includes planar surfaces, such as, for example, flats 60, as shown in FIG. 3. Flats 60 engage surface 40 in a keyed connection to resist and/or prevent rotation of crown 44 relative to receiver 16. In some embodiments, engagement of flats 60 and surface 40 prevents rotation of crown 44 relative to receiver 16 and allows axial translation of crown 44 relative to receiver 16.

Crown 44 is configured for translation within receiver 16 along surface 40. Translation of crown 44 causes surface 54 to engage a ring 104, as described herein. Surface 54 is disposed adjacent ring 104 such that axial translation of crown 44 causes crown 44 to displace ring 104 from a groove 102, as described herein. Ring 104 is disengageable from groove 102 upon engagement with crown 44, which causes a surface 106 to disengage from a projection 110 and drives ring 104 from groove 102. As such, ring 104 is movable between the contracted orientation and the expanded interference orientation in groove 124, as described herein, to prevent migration of a ring 86 from a groove 84 into a groove 124 for fixed connection of the components of bone fastener 12. Surface 54 is positioned with ring 104 to resist and/or prevent displacement of ring 104 from groove 124.

Bone fastener 12 includes a base 70. Base 70 includes a wall 72, which has a surface 74 that defines a cavity 75. Cavity 75 is configured for disposal of head 182 of screw shaft 14. Surface 74 facilitates engagement of head 182 with base 70 via a pressure and/or force fit connection. In some embodiments, surface 74 facilitates a non-instrumented assembly with base 70 and head 182 via an expandable ring, similar to ring 82 described herein. In some embodiments, base 70 may be disposed with head 182 in alternate fixation configurations, such as, for example, friction fit, pressure fit, locking protrusion/recess, locking keyway and/or adhesive. In some embodiments, base 70 is configured for rotation relative to head 182. In some embodiments, base 70 is configured for rotation in range of 360 degrees relative to head 182 to facilitate positioning of shaft 180 with tissue. In some embodiments, base 70 is configured for selective rotation in range of 360 degrees relative to and about head 182 such that shaft 180 is selectively aligned for rotation in a plane relative to receiver 16.

Figure 2:
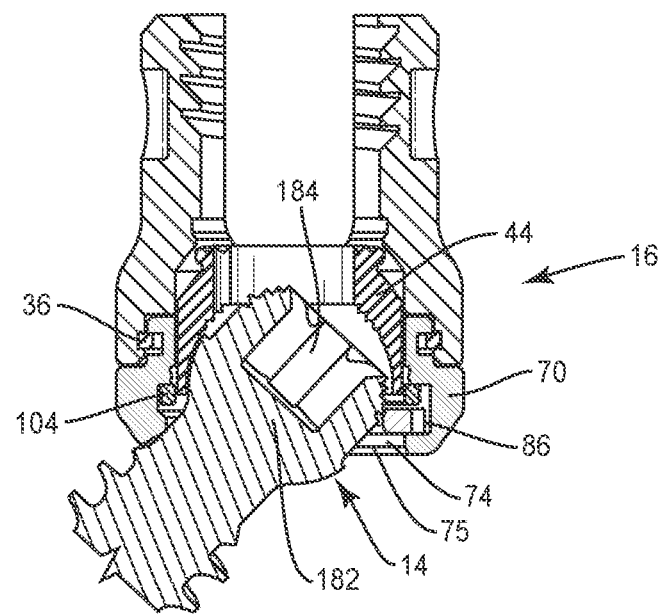
FIG. 2 is a cross section view of the components shown in FIG. 1.

Wall 72 includes a surface 76 that defines a cavity, such as, for example, a groove 78. Groove 78 is configured for disposal of ring 36 to prevent displacement of ring 36 from channel 38 and to permanently fix base 70 with receiver 16, as shown in FIG. 2, forming a base/receiver assembly 70/16. For example, alignment of groove 78 with channel 38 allows ring 36 to resiliently contract to the capture orientation, for disposal of ring 36 within groove 78 and channel 38. Ring 36 is fixed within channel 38 and groove 78. The surfaces of groove 78 resist and/or prevent disengagement of ring 36 from channel 38 and groove 78 to permanently assemble base 70 with receiver 16.

Base 70 includes a surface 82. Surface 82 defines a cavity, such as, for example, a groove 84. Groove 84 is configured for disposal of a band, such as, for example, a circumferential screw shaft ring 86, as described herein. In some embodiments, groove 84 extends about all or a portion of surface 82. Groove 84 includes a diameter D1.

Figure 6:
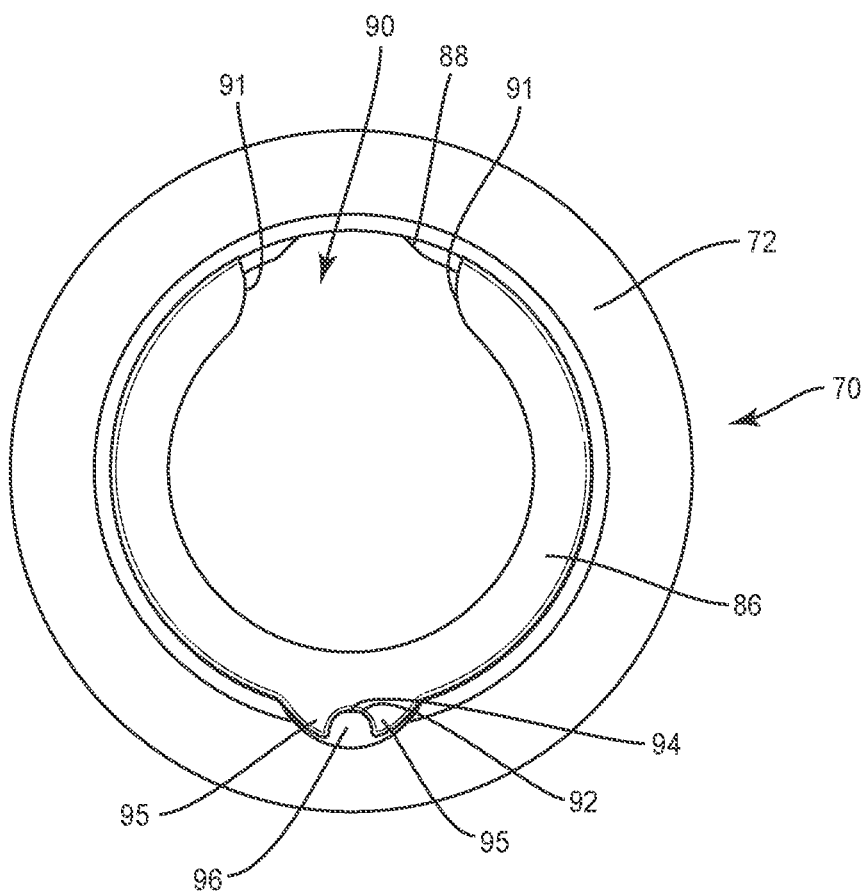
FIG. 6 is a side view of components shown in FIG. 1.
Figure 7:
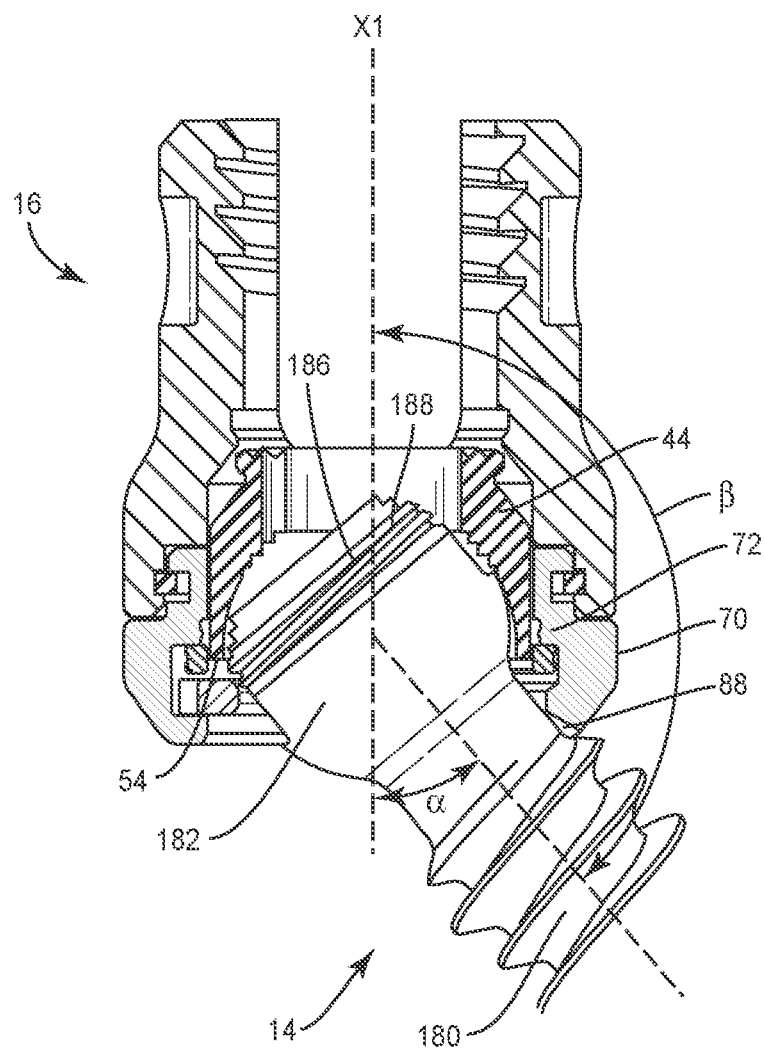
FIG. 7 is a side view, part in cross section, of the components shown in FIG. 1.

An inner surface of wall 72 defines a slot, such as, for example a recess 88, as shown in FIG. 6. Recess 88 is configured for disposal of screw shaft 14. In some embodiments, recess 88 is arcuate and/or concavely curved such that screw shaft 14 is disposable therein for movement of screw shaft 14 at an angle α as shown in FIG. 7, to facilitate a biased angle configuration at a selected angle. In some embodiments, angle α includes a selected angle in an angular range of about 30 through 60 degrees. In some embodiments, angle α is about or exactly 40 degrees relative to axis X1. In some embodiments, angulation of screw shaft 14 includes disposing receiver 16 at a sharp and/or acute angle β relative to screw shaft 14, as shown in FIG. 7, to facilitate connection with a spinal rod 200, as described herein. In some embodiments, angle β corresponds to screw shaft 14 being disposed at angle α relative to axis X1. For example, screw shaft 14 is positionable with recess 88 such that upon engagement with tissue, receiver 16 can be disposed in a non-stressed and/or relaxed configuration to facilitate receiving spinal rod 200, as described herein.

Figure 5:
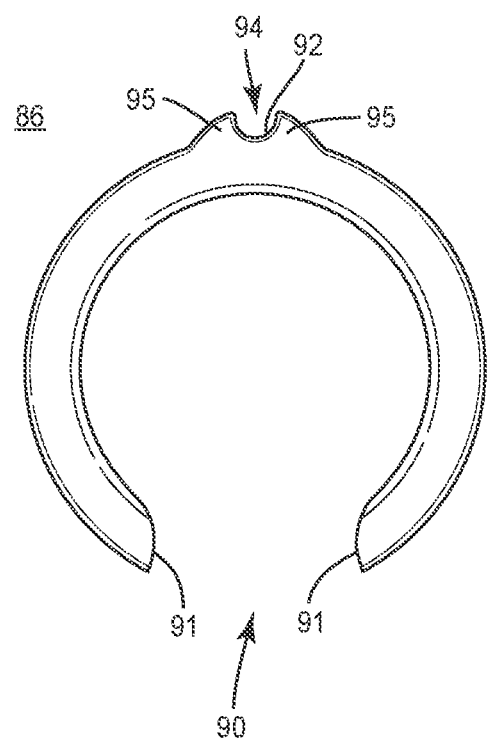
FIG. 5 is a side view of components shown in FIG. 1.

Ring 86 is configured to fix screw shaft 14 with base 70. Ring 86 includes a circumference that defines an opening 90, as shown in FIG. 5. Opening 90 is disposed between ends 91 of ring 86. Opening 90 is configured for alignment with recess 88, as shown in FIG. 6. Alignment of opening 90 and recess 88 facilitates movement of screw shaft 14 relative to receiver 16 in the angular range of motion, as described herein.

Ring 86 includes a surface 92 that defines a mating surface, such as for example, an outer recess 94, as shown in FIG. 5. Recess 94 is configured for engagement with a portion of an inner surface of base 70, such as, for example, an axial rib 96, as shown in FIG. 6. Axial rib 96 extends along base 70 parallel to axis X1. In some embodiments, axial rib 96 extends in various orientation relative to axis X1. Surface 92 defines arms 95 that capture rib 96 upon disposal of rib 96 recess 94. Engagement of rib 96 with recess 94 fixes ring 86 with base 70. Arms 95 resist and/or prevent disengagement of ring 86 from base 70. Engagement of rib 96 with recess 94 allows for axial translation of ring 86 relative to base 70 as screw shaft 14 is engaged with base 70, as described herein. Arms 95 engage rib 96 to resist and/or prevent rotation of ring 86 relative to base 70 to maintain alignment of opening 90 and recess 88.

Base 70 includes a surface 100, as shown in FIG. 2. Surface 100 defines a cavity, such as, for example, a groove 102. Groove 102 is configured for disposal of a band, such as, for example, a circumferential ring 104. Ring 104 is engageable with ring 86 to facilitate fixation of base 70 with screw shaft 14, as described herein. Ring 104 includes a surface 106 that defines an outer groove 108 configured for engagement with a surface of groove 102, as described herein. Ring 104 includes a circumference that extends between ends of ring 104. In some embodiments, the ends define an opening, such as, for example, a gap. In some embodiments, the gap is sized such that the gap has a thickness that is less than the height and the width. In some embodiments, the gap is sized to allow ring 104 to engage surface 100 by contracting circumferentially.

Groove 102 includes a projection 110. Projection 110 is configured for engagement with surface 106 of outer groove 108. Projection 110 retains ring 104 within groove 102. Projection 110 is configured to resist and/or prevent disengagement of ring 104 from groove 102. Ring 104 is disengageable from groove 102 upon engagement with crown 44, which causes surface 106 to disengage from projection 110 and drives ring 104 from groove 102, as described herein.

Groove 102 includes a diameter D2. In some embodiments, diameter D1 is equal to diameter D2, as shown in FIG. 2. In some embodiments, diameter D1 and diameter D2 are different. In some embodiments, surface 100 retains ring 102 within groove 102 and groove 102 does not include projection 110.

Base 70 includes a surface 122. Surface 122 defines a cavity, such as, for example, a groove 124 configured for disposal of ring 86 and/or ring 104 to facilitate assembly and/or fixation of base 70 with screw shaft 14. In some embodiments, groove 124 extends about all or a portion of surface 122. Groove 124 includes a circumferential channel 126 that accommodates expansion of ring 86 and/or ring 104, as described herein. Groove 124 includes a diameter D3. Diameter D3 is greater than diameter D1 and/or diameter D2. Diameter D3 is sized to allow for expansion of ring 86 and/or ring 104 therein. Grooves 84, 102, 124 are disposed in a serial orientation along axis X1, as shown in FIG. 3. In some embodiments, grooves 84, 102, 124 are disposed in spaced apart relation.

A surface 128 is disposed between groove 124 and groove 84. Surface 128 is disposed at an angle relative to axis X1 to define a ramp 130. Ramp 130 is selectively inclined to facilitate translation of ring 86 between groove 84 and groove 124, as described herein. In one example, ring 86 is engaged with screw shaft 14 for translation such that ring 86 slides along ramp 130, which directs and/or guides ring 86 from groove 84 into groove 124, and expands into a provisional capture orientation with screw shaft 14. In another example, ring 86 is engaged with ring 104 for translation such that ring 86 slides along ramp 130, which directs and/or guides ring 86 from groove 124 into groove 84, and contracts for fixed connection of the components of bone fastener 12 including permanent capture of receiver 16 and screw shaft 14. In some embodiments, surface 130 is oriented substantially perpendicular to axis X1.

Ring 86 is resiliently biased to a contracted and/or capture orientation within groove 84, as shown in FIG. 2, and expandable to an expanded orientation within groove 124, for provisional capture of screw shaft 14 with receiver 16, as described herein. Ring 86 is expandable from the contracted and/or capture orientation to the expanded orientation for assembly of screw shaft 14 with receiver 16, as shown and described for example with regard to FIGS. 8-11

Ring 104 is disposable in a contracted orientation within groove 102 and resiliently biased to an expanded interference orientation within groove 124, as shown in FIGS. 8-11. In the interference orientation, ring 104 is disposed in groove 102 and adjacent to ring 86 for abutting and/or contacting engagement therewith to resist and/or prevent translation of ring 86 from groove 84 into groove 102, and fixed connection of the components of bone fastener 12 including permanent capture of base 70 and screw shaft 14, as described herein.

Screw shaft 14 includes shaft 180 and head 182. Shaft 180 is configured to penetrate tissue, such as, for example, bone. In some embodiments, shaft 180 includes an outer surface having an external thread form. In some embodiments, the external thread form may include a single thread turn or a plurality of discrete threads. Head 182 includes a tool engaging portion 184 configured to engage a surgical tool or instrument, as described herein. In some embodiments, portion 184 includes a hexagonal cross-section to facilitate engagement with a surgical tool or instrument, as described herein. In some embodiments, portion 184 may have alternative cross-sections, such as, for example, rectangular, polygonal, hexalobe, oval, or irregular. In some embodiments, head 182 includes a surface 186 that defines a plurality of ridges 188 to improve purchase of head 182 with crown 44. Head 182 is configured for attachment with base 70 and/or receiver 16, as described herein and shown in FIGS. 8-11.

In some embodiments, base 70 and/or receiver 16 is manually engageable with screw shaft 14 in a non-instrumented assembly, as described herein. In some embodiments, manual engagement and/or non-instrumented assembly of base 70 and/or receiver 16 and screw shaft 14 includes coupling without use of separate and/or independent instrumentation engaged with screw shaft 14 components to effect assembly. In some embodiments, manual engagement and/or non-instrumented assembly includes a practitioner, surgeon and/or medical staff grasping base 70 and/or receiver 16 and screw shaft 14 and forcibly assembling the components. In some embodiments, manual engagement and/or non-instrumented assembly includes a practitioner, surgeon and/or medical staff grasping base 70 and/or receiver 16 and screw shaft 14 and forcibly snap fitting the components together, as described herein. In some embodiments, manual engagement and/or non-instrumented assembly includes a practitioner, surgeon and/or medical staff grasping base 70 and/or receiver 16 and screw shaft 14 and forcibly pop fitting the components together and/or pop fitting base 70 and/or receiver 16 onto screw shaft 14, as described herein. In some embodiments, a force in a range of 2-50 N is required to manually engage base 70 and/or receiver 16 and screw shaft 14 and forcibly assemble the components. For example, a force in a range of 2-50 N is required to snap fit and/or pop fit assemble base 70 and/or receiver 16 and screw shaft 14. In some embodiments, a force in a range of 5-10 N is required to manually engage base 70 and/or receiver 16 and screw shaft 14 and forcibly assemble the components. For example, a force in a range of 5-10 N is required to snap fit and/or pop fit assemble base 70 and/or receiver 16 and screw shaft 14. In some embodiments, screw shaft 14 is manually engaged with base 70 and/or receiver 16 in a non-instrumented assembly, as described herein, such that removal of base 70 and/or receiver 16 and screw shaft 14 requires a force and/or a pull-out strength of at least 5000 N. In some embodiments, this configuration provides manually engageable components that are assembled without instrumentation, and subsequent to assembly, the assembled components have a selected pull-out strength and/or can be pulled apart, removed and/or separated with a minimum required force. In some embodiments, spinal implant system 10 comprises a spinal implant kit, as described herein, which includes a plurality of screw shafts 14 and/or receivers 16 connectable with base 70.

Base 70 is assembled with receiver 16 in a non-instrumented to form base/receiver assembly 70/16. In some embodiments, base 70 is assembled with screw shaft 16 prior to receiver 16 being assembled with base 70. Ring 86 is disposed with base 70. Axial rib 96 is aligned with recess 94 and opening 90 is aligned with recess 88. Ring 86 is disposed with base 70 and fixed with base 70 via engagement of rib 96 and recess 94. Base 70 is engaged with receiver 16. Ring 36 is expandable and resilient between a contracted and/or capture orientation, and an expanded orientation within groove 78 and channel 38 to permanently fix base 70 with receiver 16, as shown in FIG. 2. The surfaces of groove 78 resist and/or prevent disengagement of ring 36 from channel 38 and groove 78 to permanently assemble base 70 with receiver 16.

Figure 8:
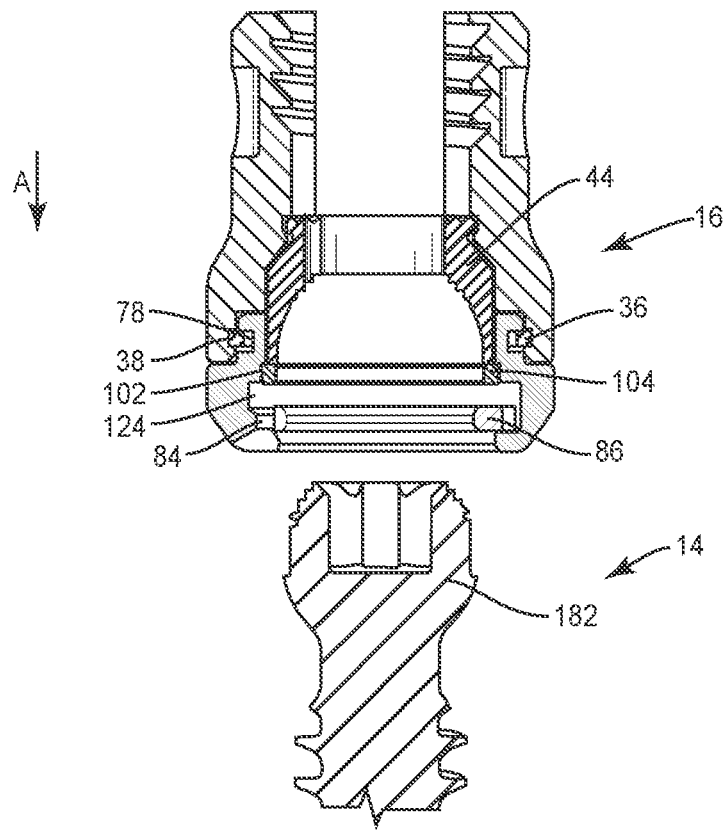
FIG. 8 is a side cross section view of the components shown in FIG. 1.
Figure 9:
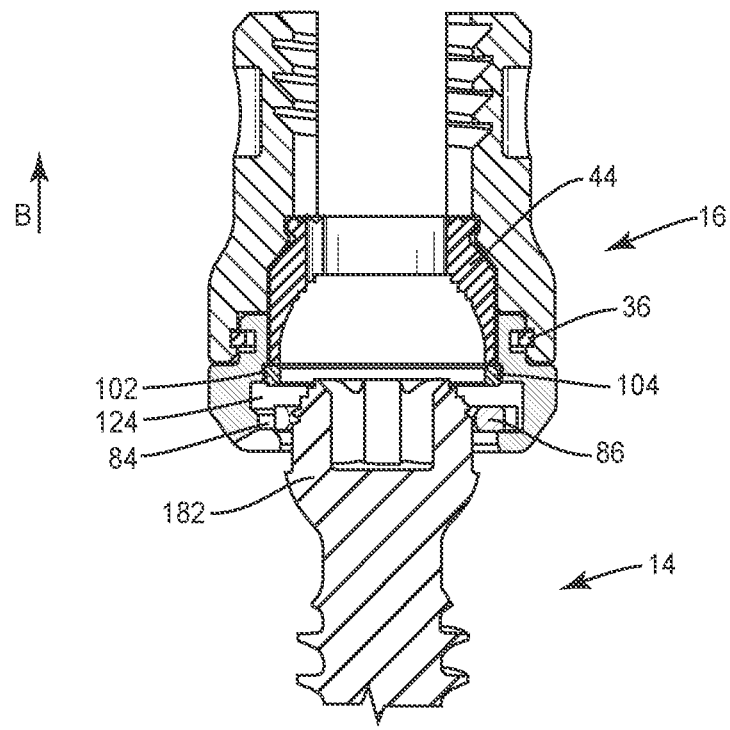
FIG. 9 is a side cross section view of the components shown in FIG. 1.
Figure 10:
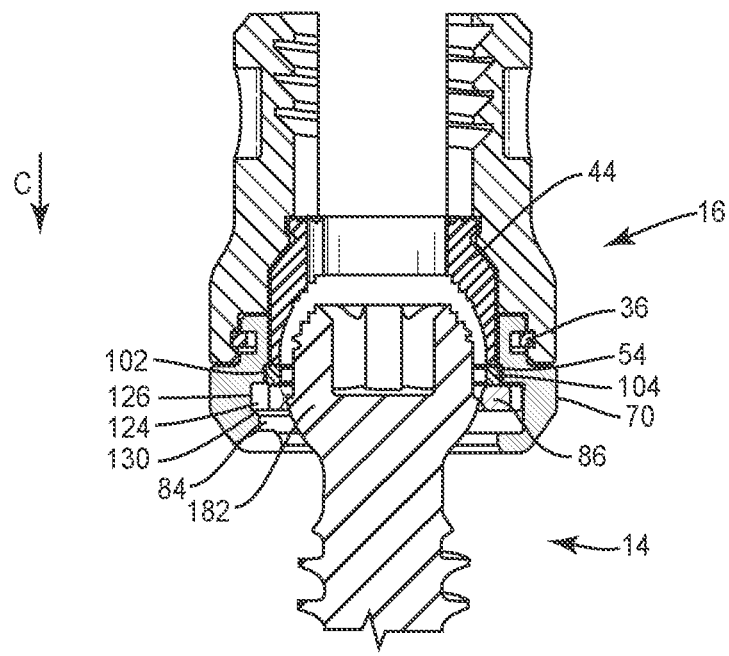
FIG. 10 is a side cross section view of the components shown in FIG. 1.

Screw shaft 14 is manually engageable, as described herein, with base/receiver assembly 70/16, as shown in FIGS. 8-10. Base/receiver assembly 70/16 is assembled with screw shaft 14 by translating base/receiver assembly 70/16, in a direction shown by arrow A in FIG. 8. Engagement of head 182 with base/receiver assembly 70/16 causes ring 86 to translate, in a direction shown by arrow B in FIG. 9, such that ring 86 is positionable and allowed to expand into groove 124 to an expanded orientation, as described herein. Diameter D3 of groove 124 is larger than diameter D1 of groove 84 to allow ring 86 to expand. Engagement of head 182 with an inner surface of ring 86 causes ring 86 to expand and slide along ramp 130 into channel 126. As head 182 translates further into base/receiver assembly 70/16, ring 86 passes over head 182 and resiliently contracts about head 182 within channel 126 to provisionally capture screw shaft 14, as shown in FIG. 10.

Figure 11:
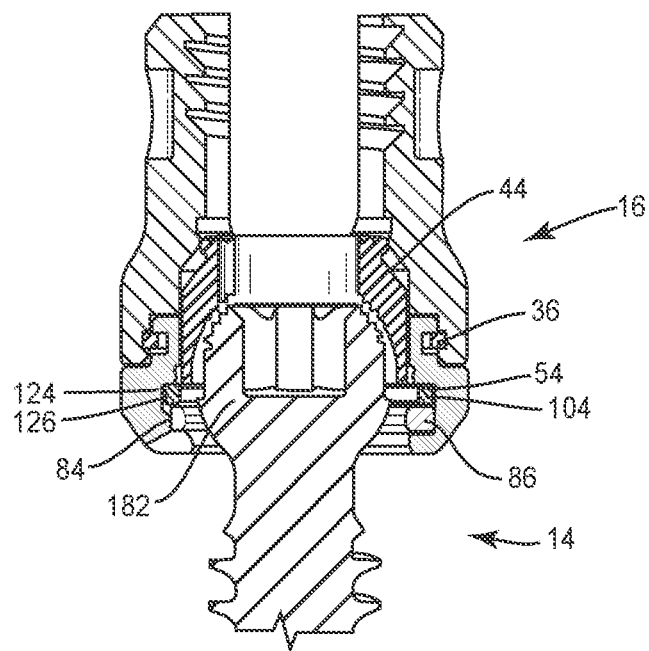
FIG. 11 is a side cross section view of the components shown in FIG. 1.

Crown 44 is manipulated, for example, via engagement by a surgical instrument to translate crown 44, in a direction shown by arrow C in FIG. 10. Surface 54 engages ring 104 such that surface 106 disengages from projection 110 and ring 104 is displaced from groove 102, as shown in FIG. 11. Ring 104 translates and engages ring 86 driving ring 86 from groove 124 into groove 84. Ring 86 axially translates along base 70 and/or slides along ramp 130 into groove 84. Ring 104 translates into groove 124 and resiliently expands to an expanded, interference orientation, as described herein. Ring 104 is oriented for abutting and/or contacting engagement with ring 86 to resist and/or prevent translation of ring 86 from groove 84 into groove 124, and fixed connection of the components of bone fastener 12 including permanent capture of base/receiver assembly 70/16 and screw shaft 14. Surface 54 is positioned with ring 104 to resist and/or prevent displacement of ring 104 from channel 126.

In assembly, operation and use, spinal implant system 10, similar to other systems and methods described herein, is employed with a surgical procedure for treating disorders of the spine, such as those described herein. In some embodiments, one or all of the components of spinal implant system 10 can be delivered as a pre-assembled device or can be assembled in situ.

A surgical treatment including spinal implant system 10 can be used for correction and alignment in stabilization of a treated section of vertebrae V. In an exemplary use, a medical practitioner obtains access to a surgical site including vertebrae V via a posterior surgical approach. In some embodiments, the surgical site may be accessed in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area.

An incision is made in the body of a patient and a cutting instrument (not shown) creates a surgical pathway for delivery and implantation of components of spinal implant system 10 with vertebrae V. A preparation instrument (not shown) can be employed to prepare tissue surfaces of vertebrae V, as well as for aspiration and irrigation of a surgical region.

Figure 12:
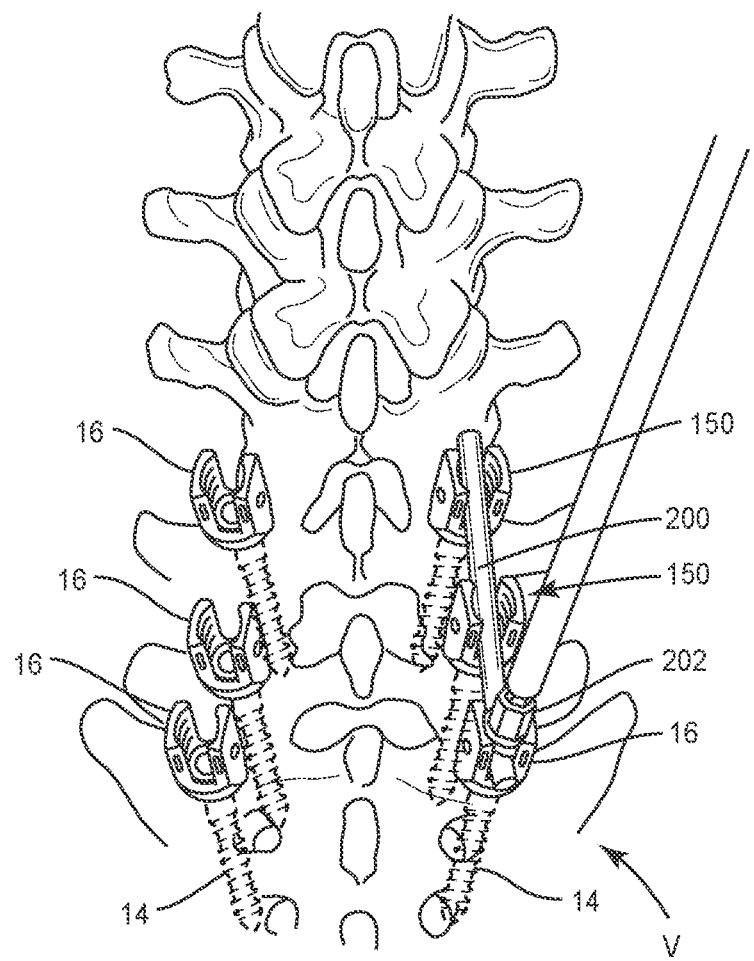
FIG. 12 is a plan view of components of one embodiment of a spinal implant system in accordance with the principles of the present disclosure disposed with vertebrae.
Figure 13:
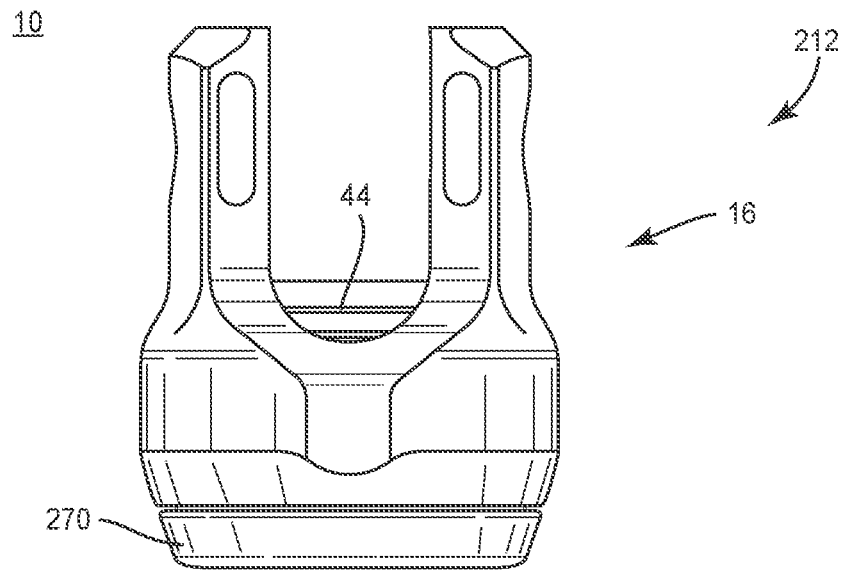
FIG. 13 is a side view of components of one embodiment of a spinal implant system in accordance with the principles of the present disclosure.
Figure 14:
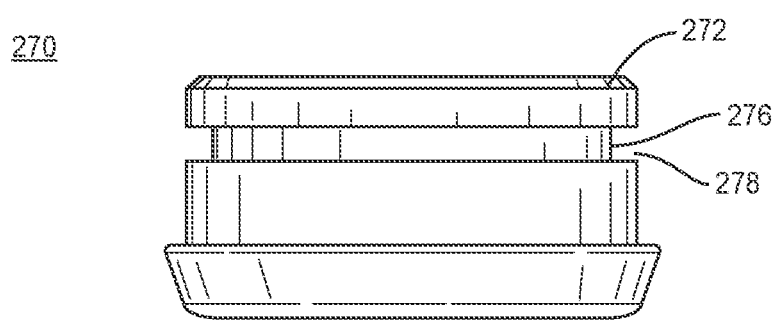
FIG. 14 is a side view of components shown in FIG. 13.

Spinal implant system 10 includes bone fasteners 12, as described herein, which are delivered to the surgical site for disposal with vertebrae V in connection with the surgical procedure. In some embodiments, one or more bone fasteners 12 are disposed in a serial and/or substantially linear orientation along vertebrae V, as shown in FIG. 12. In some embodiments, one or more bone fasteners 12 are disposed with vertebrae V in alternate orientations relative to each other, such as, for example, parallel, perpendicular, adjacent, co-axial, co-planar, arcuate, offset, staggered, transverse, angular and/or relative posterior/anterior orientations and/or at alternate vertebral levels.

Pilot holes are made in vertebrae V. Bone fastener 12 is assembled in situ or prior to implant, as described herein. In some embodiments, bone fastener 12 is assembled in a non-instrumented assembly on a back table of an operating room during a surgical procedure, as described herein. In some embodiments, bone fastener 12 is assembled in an instrumented assembly.

Screw shaft 14 is aligned with the pilot holes and fastened with the tissue of vertebrae V. In some embodiments, the bony structures of vertebrae V are disposed such that placement of bone fastener 12 includes an implant trajectory with screw shaft 14 being angled in a cephalad-caudal orientation for engagement with tissue. Such an implant trajectory of screw shaft 14 may include disposing receiver 16 at a sharp and/or acute angle 1 relative to screw shaft 14 for connection with a spinal rod 200, as described herein. In some embodiments, angle β corresponds to screw shaft 14 being disposed at a relatively larger angle α relative to axis X1. As such, the assembled components of bone fastener 12, as described herein, facilitate placement of screw shaft 14 along a selected implant trajectory and orientation of receiver 16 in a non-stressed and/or relaxed configuration to receive spinal rod 200. For example, with screw shaft 14 engaged with vertebral tissue, receiver 16 is manipulated relative to screw shaft 14 and/or to a selected angular orientation relative to screw shaft 14, for example, for disposal of screw shaft 14 with recess 88/opening 90. In some embodiments, receiver 16 is manipulable relative to screw shaft 14 to an angular limit that includes engagement of screw shaft 14 with wall 72. In some embodiments, receiver 16 is disposed at an angle 1 relative to screw shaft 14, as described herein. Opening 90 and recess 88 are aligned, as described herein, to allow screw shaft 14 to be selectively angled within opening 90 and recess 88 to angle α, as described herein. The selective angular positioning of screw shaft 14 within opening 90 and recess 88 facilitates orienting receiver 16 for receiving spinal rod 200. In some embodiments, the assembled components of bone fastener 12, as described herein, facilitate parallel orientation of lateral and contra-lateral receivers 16 of bone fasteners 12 engaged with vertebral tissue for receiving spinal rods 200.

Spinal rod 200 is shaped, contoured and/or bent to a selected configuration for a selected final lordosis of vertebrae V as attached with bone fasteners 12 in connection with the surgical procedure. Spinal rod 200 is delivered to the surgical site and oriented for alignment with implant cavities 22 of bone fasteners 12. Reduction instruments are connected with bone fasteners 12 to reduce spinal rod 200 with implant cavities 22 of bone fasteners 12. The reduction instruments manipulate vertebrae V to fully seat spinal rod 200 with bone fasteners 12. Coupling members 202 are engaged with bone fasteners 12 to fix spinal rod 200 with vertebrae V.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the fixation elements with vertebrae. In some embodiments, the agent may be HA coating. In some embodiments, the agent may include one or a plurality of therapeutic agents and/or pharmacological agents for release, including sustained release, to treat, for example, pain, inflammation and degeneration.

Upon completion of the procedure, the non-implanted components, surgical instruments and assemblies of spinal implant system 10 are removed and the incision is closed. In some embodiments, the use of microsurgical and image guided technologies may be employed to access, view and repair spinal deterioration or damage, with the aid of spinal implant system 10. The components of spinal implant system 10 can be made of radiolucent materials such as polymers. Radiomarkers may be included for identification under x-ray, fluoroscopy, CT or other imaging techniques.

In some embodiments, spinal implant system 10 can include one or a plurality of bone fasteners 12 described herein and/or fixation elements, which may be employed with a single vertebral level or a plurality of vertebral levels. In some embodiments, bone fasteners 12 may be engaged with vertebrae in various orientations, such as, for example, series, parallel, offset, staggered and/or alternate vertebral levels. In some embodiments, bone fasteners 12 may be configured as multi-axial screws, sagittal angulation screws, pedicle screws, mono-axial screws, uni-planar screws, fixed screws, anchors, tissue penetrating screws, conventional screws, expanding screws. In some embodiments, bone fasteners 12 may be employed with wedges, anchors, buttons, clips, snaps, friction fittings, compressive fittings, expanding rivets, staples, nails, adhesives, posts, connectors, fixation plates and/or post.

In one embodiment, as shown in FIGS. 13-16, surgical system 10, similar to other systems and methods described herein, includes a bone fastener 212, similar to bone fastener 12 described herein. Bone fastener 212 comprises screw shaft 14 and receiver 16, as described herein. Bone fastener 212 includes a base 270, similar to base 70 described herein, having a recess 288 disposed in alignment with an opening 290 of a screw shaft retaining ring 286 to facilitate an angular range of movement of screw shaft 14 relative to receiver 16, as described herein. In some embodiments, screw shaft 14, base 270 and receiver 16 are assembled in situ or prior to implant to form bone fastener 212, as described herein.

Receiver 16 includes a surface that defines a groove, similar to groove 34 described herein, configured for disposal of a circumferential ring, similar to ring 36 described herein. The ring is expandable and resilient between a contracted and/or capture orientation, and an expanded orientation, as described herein. Receiver 16 includes crown 44, as described herein.

Base 270 includes a wall 272, which has a surface 274 that defines a cavity 275. Cavity 275 is configured for disposal of head 182 of screw shaft 14, as described herein. Surface 274 facilitates engagement of head 182 with base 270 via a pressure and/or force fit connection, as described herein. In some embodiments, base 270 is configured for rotation relative to head 182, as described herein.

Wall 272 includes a surface 276 that defines a groove 278, similar to groove 78 described herein, configured for disposal of the ring disposed with receiver 16 to prevent displacement of the ring and to permanently fix base 270 with receiver 16, as described herein, forming a base/receiver assembly 270/16.

Figure 15:
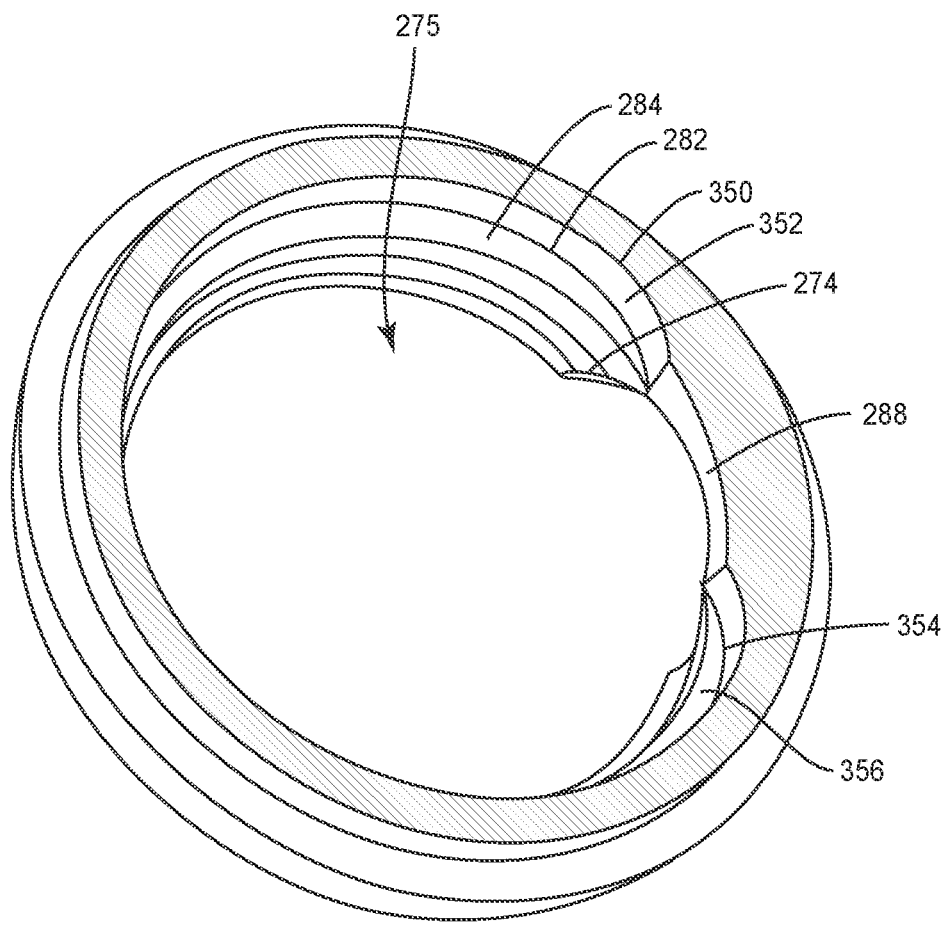
FIG. 15 is a perspective view of the component shown in FIG. 14.
Figure 16:
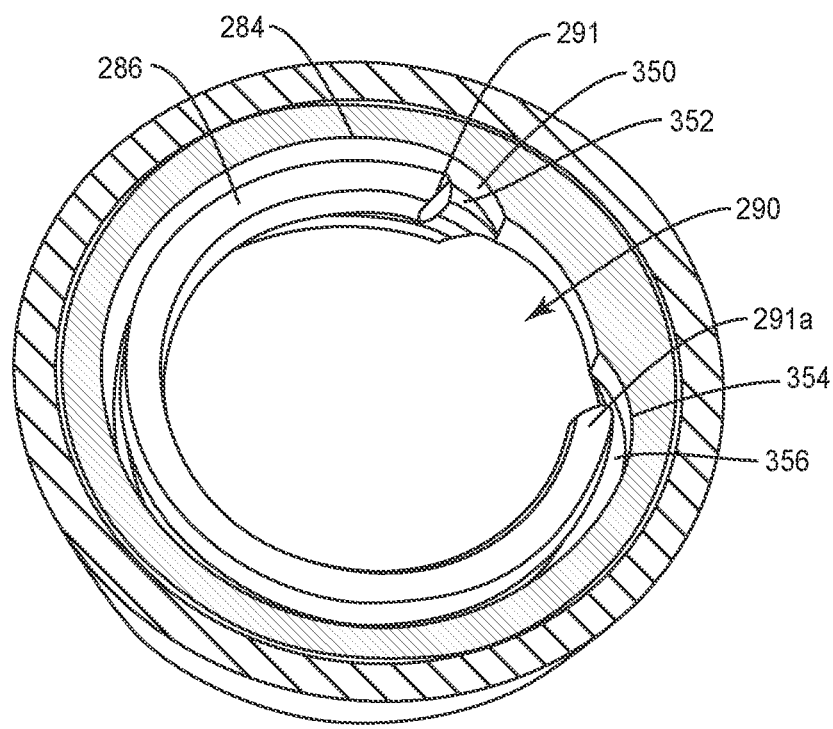
FIG. 16 is a perspective view of components of one embodiment of a spinal implant system in accordance with the principles of the present disclosure.

Base 270 includes a surface 282 that defines a cavity, such as, for example, a groove 284, as shown in FIG. 15. Groove 284 is configured for disposal of a band, such as, for example, a circumferential screw shaft ring 286, as shown in FIG. 16. In some embodiments, groove 284 extends about all or a portion of surface 282.

An inner surface of wall 272 defines recess 288, similar to recess 88 described herein. Recess 288 is configured for disposal of screw shaft 14, as described herein. In some embodiments, recess 288 is arcuate and/or concavely curved such that screw shaft 14 is disposable therein for movement of screw shaft 14 at an angle as described herein, to facilitate a biased angle configuration at a selected angle.

Ring 286 is configured to fix screw shaft 14 with base 270, as described herein. Ring 286 includes a circumference that defines an opening 290, as shown in FIG. 16. Opening 290 is disposed between ends 291, 291a of ring 286. Opening 290 is configured for alignment with recess 288. Alignment of opening 290 and recess 288 facilitates movement of screw shaft 14 relative to receiver 16 in the angular range of motion, as described herein.

Groove 284 includes a surface 350 that defines a mating surface, such as, for example, a notch 352, as shown in FIGS. 15 and 16. Groove includes a surface 354 that defines a mating surface, such as, for example, a notch 356. Notches 352, 356 are disposed on opposite sides of recess 288. End 291 is configured for disposal with notch 352 and end 291a is configured for disposal with notch 356, as shown in FIG. 16. In the expanded orientation, ends 291, 291a engage surfaces 350, 354 to fix ring 286 with base 270 for assembly, as described herein. Surfaces 350, 354 resist and/or prevent disengagement of ring 286 from base 270. Engagement of ends 291, 291a with surfaces 350, 354 of notches 352, 356 allows for axial translation of ring 286 relative to base 270 as screw shaft 14 is engaged with base 720, as described herein. Ends 291, 291a engage surfaces 350, 354 to resist and/or prevent rotation of ring 286 relative to base 270 to maintain alignment of opening 290 and recess 288.

Base 270 includes a groove 302, similar to groove 102 described herein, configured for disposal of a circumferential ring, similar to ring 104 described herein. The ring is engageable with screw shaft ring 286 to facilitate fixation of base 270 with screw shaft 214, as described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A bone fastener comprising:
   a first member defining an implant cavity and a first groove;
   a first band disposable in the first groove;
   a base connectable with the first member and engageable with the first band, the base defining a second groove and a slot;
   a second band disposable in the second groove and defining an opening aligned with the slot;
   a second member connectable with the base and engageable with the second band, the second member being configured to penetrate tissue,
   the opening being aligned with the slot to facilitate an angular range of movement of the second member relative to the first member; and
   a third band disposed with the base expandable between a contracted orientation and an interference orientation to fix connection of the base and the second member.

2. A bone fastener as recited in claim 1, wherein the second member is disposable in the slot to a selected angulation relative to the first member.

3. A bone fastener as recited in claim 2, wherein the selected angulation includes an angular range of about 30 through about 60 degrees relative to a longitudinal axis of the first member.

4. A bone fastener as recited in claim 2, wherein the selected angulation includes an angle of about 40 degrees relative to a longitudinal axis of the first member.

5. A bone fastener as recited in claim 1, wherein the slot includes an arcuate recess disposed with an inner surface of the base.

6. A bone fastener as recited in claim 1, wherein the second band is fixed with the second groove.

7. A bone fastener as recited in claim 1, wherein the second band includes a first mating surface engageable with a second mating surface of the second groove, the mating surfaces being engageable to fix the second band with the second groove.

8. A bone fastener as recited in claim 7, wherein the mating surfaces are engageable such that the second band axially translates relative to the base.

9. A bone fastener as recited in claim 7, wherein the mating surfaces are engageable to resist and/or prevent rotation of the second band relative to the base.

10. A bone fastener as recited in claim 1, wherein the second band defines an outer recess engageable with an axial rib of the second groove to fix the second band with the second groove.

11. A bone fastener as recited in claim 1, further comprising a part disposed within the implant cavity and having a distal face engageable with the third band to fix the third band adjacent the second band.

12. A bone fastener as recited in claim 1, wherein the second band is engageable with a mating surface of the second groove, to rotationally fix the second band with the second groove.

13. A bone fastener comprising:
    a first member defining an implant cavity and a first groove;
    a first band disposable in the first groove;
    a part disposed within the implant cavity;
    a base connectable with the first member and engageable with the first band, the base defining a second groove and a slot;
    a second band disposable in the second groove and defining an opening aligned with the slot;
    a second member connectable with the base and engageable with the second band, the second member being configured to penetrate tissue; and
    a third band disposed with the base, the part being engageable with the third band to fix the base with the second member,
    the opening being aligned with the slot to facilitate an angular range of movement of the second member relative to the first member.

14. A bone fastener as recited in claim 13, wherein the second band is expandable between a provisional capture orientation and an expanded orientation, and the third band being expandable between a contracted orientation and an interference orientation to fix connection of the base and the second member.

15. A bone fastener as recited in claim 13, wherein the part includes a distal face engageable with the third band to fix the third band adjacent the second band.

16. A bone fastener as recited in claim 13, wherein the part includes a crown.

17. A bone fastener comprising:
    a spinal rod receiver defining a first groove;

a first band disposable in the first groove;
a base connectable with the receiver and engageable with the first band, the base defining a second groove and a slot;
a second band disposable in the second groove and defining an opening aligned with the slot;
a screw shaft connected to a head, the head connectable with the base and engageable with the second band; and
a third band disposed with the base expandable between a contracted orientation and an interference orientation to fix connection of the base and the head,
the opening being aligned with the slot and the screw shaft being movable in the slot to a selected angulation relative to the receiver.

18. A bone fastener as recited in claim 17, wherein the selected angulation includes an angular range of about 30 through about 60 degrees relative to a longitudinal axis of the receiver.

19. A bone fastener as recited in claim 17, wherein the selected angulation includes an angle of about 40 degrees relative to a longitudinal axis of the receiver.

* * * * *